US008839785B2

(12) United States Patent
Castiglione et al.

(10) Patent No.: US 8,839,785 B2
(45) Date of Patent: Sep. 23, 2014

(54) RESPIRATOR HARNESS HAVING COLLAPSIBLE HEAD CRADLE

(75) Inventors: David M. Castiglione, Hudson, WI (US); William A. Mittelstadt, Woodbury, MN (US); Thomas W. Holmquist-Brown, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1010 days.

(21) Appl. No.: 12/721,036

(22) Filed: Mar. 10, 2010

(65) Prior Publication Data
US 2011/0220115 A1 Sep. 15, 2011

(51) Int. Cl.
*A62B 17/04* (2006.01)
*A62B 18/00* (2006.01)
*A62B 18/08* (2006.01)
*A61M 16/06* (2006.01)

(52) U.S. Cl.
CPC ................................. *A61M 16/0683* (2013.01)
USPC ................................ 128/201.24; 128/207.11

(58) Field of Classification Search
USPC ............. 128/201.24, 206.27, 207.11, 207.17; 2/416, 420
See application file for complete search history.

(56) References Cited

U.S. PATENT DOCUMENTS

| | | | |
|---|---|---|---|
| 4,414,973 A | 11/1983 | Matheson | |
| 4,555,815 A | 12/1985 | Walther | |
| 4,934,361 A | 6/1990 | Michel et al. | |
| 5,069,205 A | 12/1991 | Urso | |
| 5,181,507 A | 1/1993 | Michel et al. | |
| 5,464,010 A * | 11/1995 | Byram | 128/207.11 |
| 5,488,948 A | 2/1996 | Dubruille et al. | |
| 5,592,937 A | 1/1997 | Freund | |
| 6,012,164 A | 1/2000 | Deal, III | |
| 6,039,045 A | 3/2000 | Bertheau et al. | |
| 6,453,475 B1 | 9/2002 | Johnson | |
| 6,497,232 B2 | 12/2002 | Fecteau et al. | |
| 6,536,435 B1 | 3/2003 | Fecteau et al. | |
| 6,715,490 B2 | 4/2004 | Byram | |
| 6,732,733 B1 | 5/2004 | Brostrom et al. | |

(Continued)

FOREIGN PATENT DOCUMENTS

GB 2162889 A 2/1986
JP 3785431 6/2006

(Continued)

OTHER PUBLICATIONS

International Search Report for Application No. PCT/US2011/026798 dated Nov. 25, 2011.

*Primary Examiner* — Nathan R Price
(74) *Attorney, Agent, or Firm* — Karl G. Hanson

(57) ABSTRACT

A respirator 10 that includes a harness 12 and a mask body 14. The harness 12 has one or more straps 21 and a head cradle 16 that is joined to the one or more straps 21 and that includes first and second laterally-extending members 18, 20 and a latch 26. The latch 26 is able to secure the laterally-extending members 18, 20 in a spaced apart first open position to allow for placement on a person's head and is able to disengage so that the members 18, 20 can move to a second collapsed position to allow for off-the-face storage. The harness is beneficial in that it can be quickly removed from the wearer's head and can be conveniently disposed behind the wearer's neck when the wearer wants to temporarily displace the mask body from their face.

23 Claims, 2 Drawing Sheets

(56) References Cited

U.S. PATENT DOCUMENTS

| | | |
|---|---|---|
| 7,841,026 B2 | 11/2010 | Makris |
| 2002/0088466 A1 | 7/2002 | Brostrom et al. |
| 2003/0178026 A1 | 9/2003 | Byram |
| 2004/0003810 A1 | 1/2004 | Templeton et al. |
| 2005/0155604 A1 | 7/2005 | Ging et al. |
| 2006/0032504 A1* | 2/2006 | Burton et al. ............ 128/207.11 |
| 2006/0162729 A1 | 7/2006 | Ging et al. |
| 2006/0196511 A1* | 9/2006 | Lau et al. ................. 128/207.11 |
| 2006/0225740 A1 | 10/2006 | Eaton et al. |
| 2007/0044797 A1 | 3/2007 | Ho |
| 2007/0186931 A1* | 8/2007 | Zollinger et al. ........ 128/207.11 |
| 2008/0066759 A1 | 3/2008 | Howard et al. |
| 2008/0190432 A1 | 8/2008 | Blochlinger |
| 2008/0196727 A1 | 8/2008 | Ho et al. |
| 2008/0230069 A1 | 9/2008 | Valcic et al. |
| 2009/0178680 A1 | 7/2009 | Chang |
| 2009/0217926 A1 | 9/2009 | Hine et al. |
| 2009/0250065 A1 | 10/2009 | Omura et al. |

FOREIGN PATENT DOCUMENTS

| | | |
|---|---|---|
| RU | 2171122 | 7/2001 |
| WO | 96/40370 | 12/1996 |
| WO | 2004/041341 | 5/2004 |
| WO | 2005/118042 | 12/2005 |

* cited by examiner

RESPIRATOR HARNESS HAVING COLLAPSIBLE HEAD CRADLE

The present invention pertains to a respirator head cradle that can be easily collapsed from its in-use position to allow the respirator harness to rest comfortably behind a wearer's neck when the mask body is placed in an off-the-face storage condition.

BACKGROUND

Respirators are commonly provided with harnesses to support the mask body on a wearer's face during use. Some respirator harnesses are provided with a "drop-down" assembly that allows the mask body to be conveniently disposed beneath a wearer's chin when not in use. Occasions frequently arise in the workplace which require the respirator wearer to temporarily displace the mask body from their face when they are away from a contaminated area. The wearer may, for example, temporarily leave the contaminated area for a short time period to briefly speak to another person. To satisfy the need for easy mask body displacement and temporary-off-the-face storage beneath the chin, respirator designers have created these "drop-down" facemask assemblies for this purpose.

U.S. Pat. No. 6,715,490 to Byram discloses a drop-down respirator that has a head cradle or crown member and a pair of straps for supporting the mask body on the wearer's head. To provide temporary off-the-face storage, the Byram harness uses a substantially flat, flexible strap and an element that contains a curved elongated slot. When the flat strap is threaded through the curved elongated slot, the curved configuration of the slot causes the flat strap to be deformed into a curved configuration. This strap deformation allows it to frictionally engage the element, which in turn allows the respirator body to be incrementally withdrawn from the wearer's face so that it can be temporarily stored beneath the wearer's chin and can be conveniently repositioned over the nose and mouth by simply pulling on the free ends of each strap.

U.S. Pat. No. 6,732,733 to Brostrom et al. has a carriage that is disposed on the mask body and that is adapted for engaging the straps that are threaded through four spaced apart guide members on the carriage. The guide members cause the straps to take on a cross-configuration with respect to the four engagement points. This structure enables the mask body to be retained in a second position, dropped down beneath the face of the wearer, without removing the support harness from the wearer's head.

U.S. Pat. No. 6,497,232 to Fecteau et al. describes a quick-release mechanism and headpiece or crown member for use with the respirator. The headpiece is joined to a pair of straps for supporting the mask body on the wearer's head. The quick-release mechanism has a cam latch that is pivotally attached to a yoke to control the tension in an upward tension strap. In the latched position, the upper tension strap traverses the yoke to support and seal the respirator mask against the wearer's face. In the unlatched position, the upper tension straps loosely support the mask body below the chin of the wearer in a parked position. Fecteau et al. relies on the inclusion of a cam latch to move the mask from its in-use position to is parked position.

Thus, in the known drop-down harness assemblies described in the Byram, Brostrom et al., and Fecteau et al. patents, the crown members remain on the wearer's head while the mask body becomes dropped down beneath the chin.

SUMMARY OF THE INVENTION

Unlike known drop-down respirators, the present invention does not rely on movement of the mask relative to the straps to provide for temporary displacement beneath the chin. In the present invention, the straps do not need to be readjusted or refastened when placing the mask body back over the wearer's nose and mouth. The convenience of the present invention relies on a collapsible crown member or head cradle to provide for a temporary off-the-face-storage. As indicated above, known drop-down respirators have moved the mask body relative to the harness straps to provide for the temporary off-the-face storage.

In brief summary, the present invention provides a respirator that comprises: (a) mask body; and (b) a harness that comprises (i) one or more straps, and (ii) a head cradle that is joined to the one or more straps and that includes first and second laterally-extending members and a latch. The latch is able to secure the laterally-extending members in a spaced apart first open position to allow for placement on a person's head and is able to disengage so that the members can move to a second collapsed position to allow for off-the-face storage.

The present invention also provides a respirator that comprises: (a) a mask body; and (b) a harness that comprises: (i) one or more straps; and (ii) a head cradle that is joined to the one or more straps and that includes first and second laterally-extending members and a means for securing the laterally-extending members in a spaced apart first open position to allow for placement of the cradle on a person's head and for disengaging the members to allow for movement to a second collapsed position for off-the-face storage of the mask body.

The present invention additionally provides a harness that may be used to support a mask body on a person's face, which harness comprises: (a) a head cradle that has: (i) first and second laterally extending members; and (ii) a means for allowing the laterally extending members to move from a first desired location to a second location; and (b) one or more straps that are joined to the head cradle.

The present invention further provides a method of placing a mask body from an on-the-face in-use condition to an off-the-face temporary storage condition, which method comprises: (a) collapsing a head cradle from an on-the-head first position; and (b) placing the collapsed head cradle into a second position behind the neck so that the mask body is supported beneath the chin.

The present invention differs from known drop-down harness assemblies in that it has first and second laterally-extending members that can be moved from a spaced apart first open position to a second collapsed position. When in the second collapsed position, the laterally-extending members may reside closer together so that the cradle can be comfortably positioned behind the wearer's neck. The collapsed cradle enables the mask body to be conveniently stored in an off-the-face storage position in front of the wearer's chest. Known harnesses had not previously allowed for the crown member or cradle to be collapsible. As such, the crown member or cradle could not be comfortably positioned behind the wearer's neck when the mask wearer wanted it to displace the mask body from the facial in-use position. Respirator designers therefore relied on movement of the mask body through the harness straps to provide for the temporary off-the-face storage as described above in the Byram, Brostrom et al., and Fecteau patents.

GLOSSARY

The terms set forth below will have the meanings as defined:

"harness" means a structure or combination of parts that assists in supporting a mask body on a wearer's face;

"head cradle" means a part or combination of parts that is/are configured for being worn on a person's head for supporting another device;

"latch" means a part or combination of parts that allows one or more members to be temporarily joined together in a relatively secured or fixed position;

"lateral" means across or from side-to-side;

"mask body" means a structure that can fit at least over the nose and mouth of a person and that helps define an interior gas space separated from an exterior gas space;

"respirator" means a device that is worn by a person to filter air before the air enters the person's respiratory system;

"strap" means a strip of material(s) (typically of uniform width) with sufficient strength to support another item by itself or in conjunction with other strap(s);

DETAILED DESCRIPTION OF PREFERRED EMBODIMENTS

In practicing the present invention, a respirator is provided that has a harness that allows for convenient off-the-face storage of the mask body. Rather than move the mask body relative to the harness straps as has been done in the past, the present invention provides for a collapsible head cradle that can rest behind the wearer's neck so that the mask body can be placed in an off-the-face storage position in front of the wearer's chest. To provide for such off-the-face storage, the harness comprises a head cradle that includes first and second laterally-extending members and a latch. The latch allows the laterally-extending members to be secured together in an open position for placement on a person's head. The latch also allows the members to be disengaged so that they can move to a second collapsed position where they can be conveniently disposed behind the wearer's neck.

Figure 1:
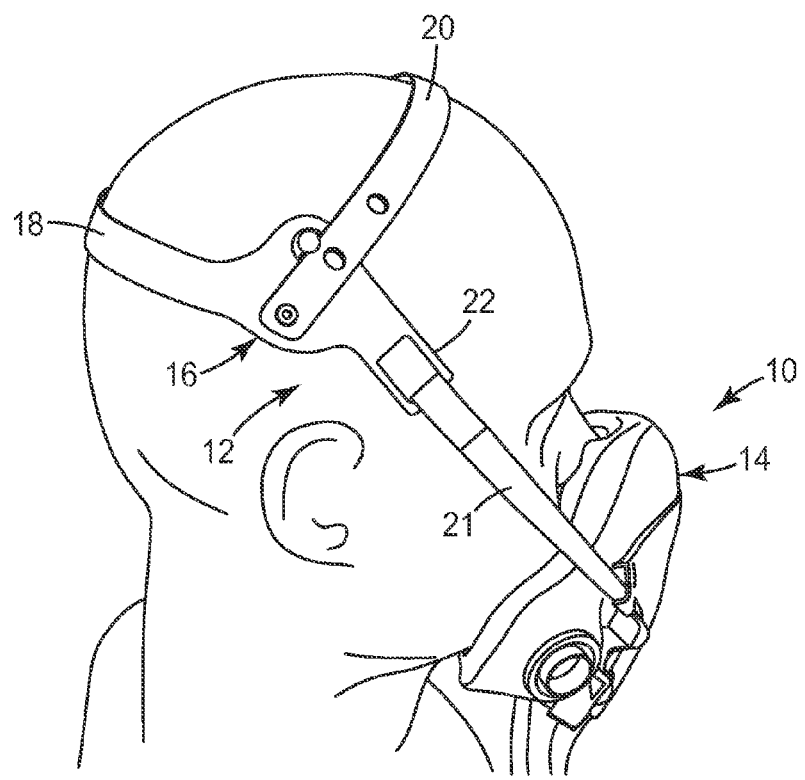
FIG. 1 is a perspective view of a respirator 10, in accordance with the present invention, disposed on a person's face in an in-use position.

FIG. 1 shows a respirator 10 that comprises a harness 12 and a mask body 14. The harness 12 includes a crown member or cradle 16, which comprises a first laterally-extending member 18 and a second laterally-extending member 20. A strap 21 is attached to the head cradle 16 at a buckle 22. A strap 21 may be attached from the mask body 14 to the head cradle 16 on each side of the cradle 16 and mask body 14. The straps 21 may be adjustable at one or more ends. The straps can be joined on each side of the cradle 16 using the buckles 22.

Figure 2:
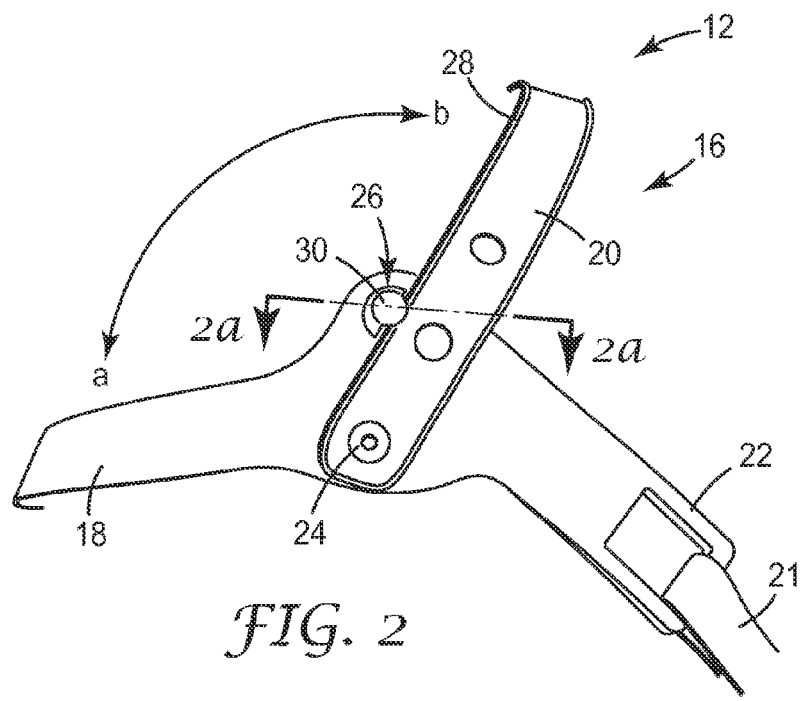
FIG. 2 is an enlarged view of a head cradle 16, which view shows an example of a latch 26 that may be used on a harness 12 in accordance with the present invention.
Figure 2A:
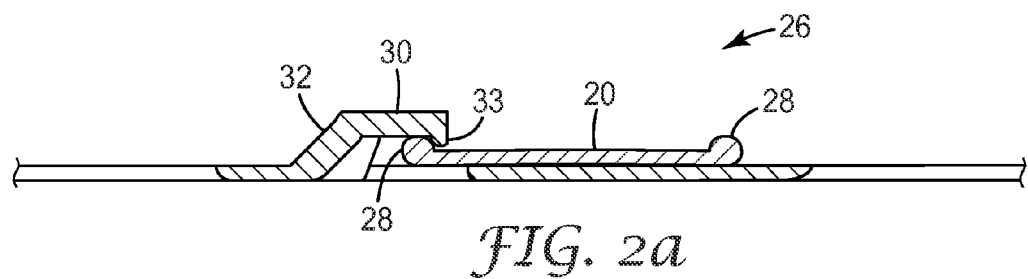
FIG. 2a is a cross-section of the latch 26 taken along lines 2a-2a of FIG. 2.

FIG. 2 illustrates the head cradle 16 in an enlarged condition. As shown, the cradle 16 joins the first and second laterally-extending members 18 and 20 together at a pivot point 24. The pivot point 24 allows the first and second laterally-extending members 18, 20 to rotate about the point relative to one another in the a and b directions. The pivot point may be provided by a rivet or other suitable means. A latch 26 may be provided in a convenient location on the cradle 16 to prevent the rotation of the first member 18 relative to the second member 20. As shown in FIG. 2a, the second member 20 may comprise a small bead 28 that is molded along the perimeter. This bead 28 engages an undercut button 30 that holds the laterally-extending member 20 in position. The undercut button 30 may have a tapered top surface 32 that allows member 20 to slide over the undercut button 30 without being caught on it when being rotated in the b direction. The slightly raised bead 28 engages the undercut button 30 when the member 20 is moved in the b direction past the ridge 33. When the raised bead 28 of the laterally-extending member is so placed within the undercut button 30, the engagement allows the laterally-extending member 20 to be temporarily held in place without rotational movement relative to the laterally-extending member 18. To place the mask body 14 in an off-the-face position, the wearer simply grasps the laterally-extending member 20 and flips it forward in the b direction with their thumbs to release it from the undercut button 30. The laterally-extending member 20 is then rotated in the counterclockwise a direction so that it is more closely disposed to, or overlapping with, the first laterally-extending member 18.

Figure 3:
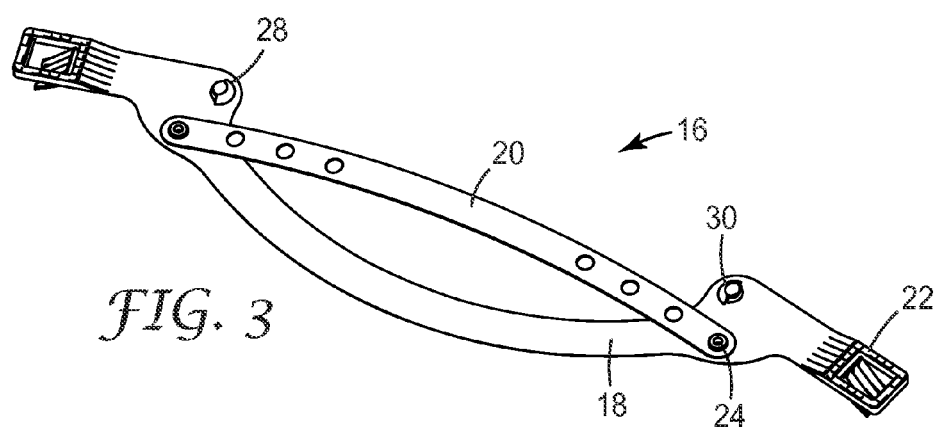
FIG. 3 is a perspective view of the head cradle 16 in a closed position.
Figure 4:
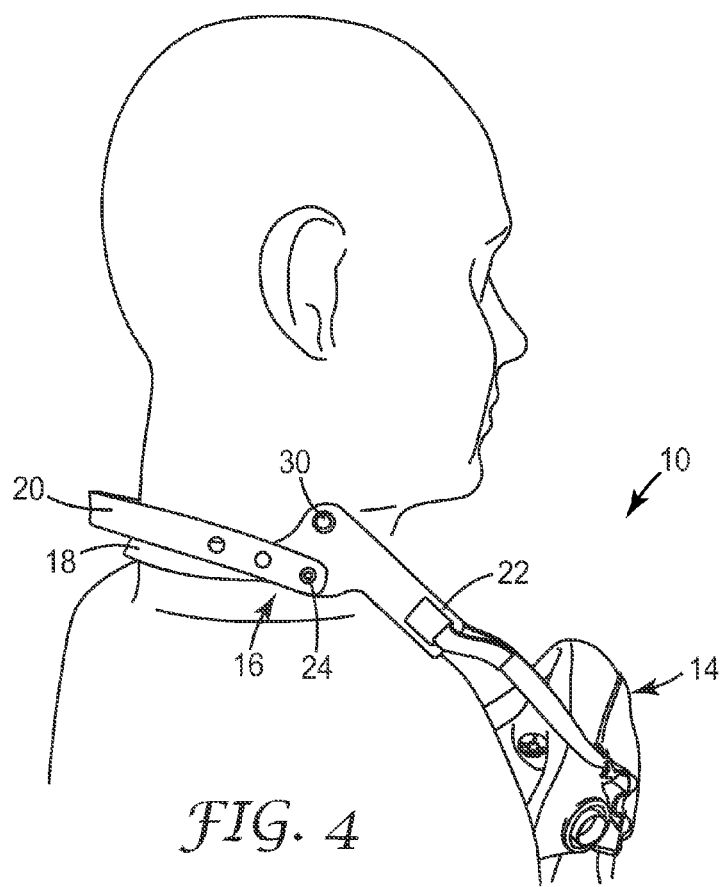
FIG. 4 is a perspective view of the respirator 10, showing the mask body 14 in an off-the-face storage position and showing the head cradle 16 in a collapsed condition around the wearer's neck.

FIG. 3 shows the laterally-extending members in a position for off-the-face storage. As shown, the laterally-extending member 20 is disengaged from the latch 26. Members 18 and 20 therefore are closer together and therefore can be comfortably placed behind the wearer's neck. As shown in FIG. 4, a major surface of each laterally-extending member 18 or 20 faces a major surface of the other laterally-extending member in an overlapping relationship. The cradle 16 may then be lowered from the head to rest on the back of the neck as shown in FIG. 4. One or more of the laterally-extending members may be provided with a curvature that extends along the length of the laterally-extending member. The curvature may allow for conformability about an axis that is normal to the lengthwise dimension of the lateral member. As such, the imparted curvature may further enhance fit upon the wearer's head and comfort behind the wearer's neck. The imparted curve may have a radius of about 8 to 20 centimeters (cm).

The cradle 16 may be made from a variety of materials, typically plastics such as polypropylene, polyethylene, polyvinyl chloride, and ABS (Acyrlonitrile Styrene Butadiene). Straps too may be made from various materials including woven or braided polyester, nylon, or cotton fibers (or blends thereof) and natural rubber/polyisoprene/urethane/neoprene rubber strands. Typically, the straps are taken in a flat shape with a first and second major surfaces. The straps typically are about 1 to 2 centimeters (cm) wide and may be up to 60 cm long. The straps may be made from an elastic material to allow the mask body to exert firm pressure upon a wearer's face when worn. The latch may take on other forms besides the undercut button illustrated in the drawings. The latch, for example, could be in the form of one or more snap buttons disposed on each side of the cradle when the wearer desires to collapse the head cradle, the wearer would only need to unsnap the button on each side. Additionally, a small ridge could be molded into the rear laterally-extending member to help keep the forward laterally-extending member in the open position by acting as a slight catch that holds the members in position. In yet another embodiment, spring-loaded ball bearings could be used to hold the laterally-extending members in position relative to each other. The spring-loaded ball bearing would engage in a recess in the other member. Or instead of using a separate spring-loaded ball bearing, the plastic parts could be molded with features that create a similar action. The features would elastically deform to create the same affect as the spring-loaded ball bearing. Additionally, hook and loop type fasteners, or a tab that deforms and bends to hook around the edge of the laterally-extending member also could be used in the present invention.

EXAMPLE

A harness that resembles the harness illustrated in the drawings was made from a cradle that had two integral buckles. Two elastic straps were joined to two buckles that could be hooked together behind the wearer's neck. The harness was then attached to a respirator mask body. The cradle was made from 2 separate injection molded parts to form them into shapes that readily conformed to a wearer's head. One member was molded flat for ease of manufacturing and to allow for conformability about an axis normal to their lengthwise dimension. The conformability enabled the member to be adapted into a curved form to improve conformance to a wearer's head. The other component was molded into a curve having a radius of about 12 cm, which gave a good combination of ease of manufacturing and conformance to the head. The cradle also included a pivot button that allowed relative motion between the two laterally-extending members. This relative motion allowed the members to collapse into the storage position. During use, the first member was retained to the second member by snapping it onto a ridge on the underside of an undercut button, thus forming the on-the-head cradle shape. The cradle was then maintained in this locked open position through a bead on the second member that engages the ridge of the first member. When the user put the cradle on their skull, it maintained this open shape for use. When the user wanted to hang the mask around their neck for storage, they unhooked the second member from the undercut button on the first member. The second member was then rotated towards the first member to collapse the cradle. The cradle was made from polypropylene thermoplastic. The plastic had enough strength to not deflect too much for the intended use but still remain flexible and sturdy.

This invention may take on various modifications and alterations without departing from its spirit and scope. Accordingly, this invention is not limited to the above-described but is to be controlled by the limitations set forth in the following claims and any equivalents thereof.

This invention also may be suitably practiced in the absence of any element not specifically disclosed herein.

All patents and patent applications cited above, including those in the Background section, are incorporated by reference into this document in total. To the extent there is a conflict or discrepancy between the disclosure in such incorporated document and the above specification, the above specification will control.

What is claimed is:

1. A respirator that comprises:
   (a) a mask body; and
   (b) a harness that comprises:
      (i) one or more straps; and
      (ii) a head cradle that is joined to the one or more straps and that includes first and second laterally-extending members and a latch, the first and second laterally-extending members resting on a wearer's head when the harness is placed thereon and the latch is engaged, the engaged latch securing the first and second laterally-extending members in a spaced apart first open position to allow for placement of each of the laterally-extending members on the wearer's head when the respirator is being used, a disengaged latch allowing the first and second laterally-extending members to move to a second collapsed position to allow for an off-the-face storage.

2. The respirator of claim 1, wherein the first and second laterally-extending members are capable of rotating about a point relative to one another.

3. The respirator of claim 2, wherein the point where the first and second laterally-extending members are capable of rotating comprises a rivet.

4. The respirator of claim 1, wherein the latch includes an undercut button that comprises a tapered top surface.

5. The respirator of claim 4, wherein at least one of the first and second laterally-extending members includes a bead that is molded along a perimeter of the laterally-extending member that includes the bead.

6. The respirator of claim 5, wherein the undercut button includes a ridge that engages the bead on the laterally-extending member when the latch is in a closed position.

7. The respirator of claim 6, wherein the latch can be manually disengaged by a wearer.

8. The respirator of claim 7, wherein the laterally-extending members can be moved closer together when disengaged from the latch.

9. The respirator of claim 1, wherein one or more of the laterally-extending members is provided with a curvature that extends along a length of the laterally-extending member.

10. The respirator of claim 9, wherein the curvature has a radius of 8 to 20 centimeters.

11. The respirator of claim 10, wherein the head cradle comprises a plastic selected from the group consisting of polypropylene, polyethylene, polyvinylchloride, and acrylonitrile-styrene-butadiene.

12. The respirator of claim 1, wherein the harness comprises first and second straps that are 1 to 2 centimeters wide and up to 60 centimeters long.

13. The respirator of claim 1, wherein a major surface of the first laterally-extending member faces a major surface of the second laterally-extending member in an overlapping relationship when in the second collapsed position.

14. A method of placing the mask body of the respirator of claim 1 from an on-the-face in-use condition to an off-the-face temporary storage condition, which method comprises:
   (a) collapsing the head cradle from an on-the-head first position; and
   (b) placing the collapsed head cradle into a second position behind the neck so that the mask body is supported beneath the chin.

15. The method of claim 14, wherein the head cradle may be collapsed by manually moving the first and second laterally-extending members closer to each other.

16. A respirator that comprises:
   (a) a mask body; and
   (b) a harness that comprises:
      (i) one or more straps; and
      (ii) a head cradle that is joined to the one or more straps and that includes first and second laterally-extending members and a means for securing the first and second laterally-extending members in a spaced apart first open position to allow for placement of the cradle on a person's head and for manually disengaging the first and second laterally-extending members to allow for movement to a second collapsed position for off-the-face storage of the mask body, wherein the first and second laterally-extending members rest upon a wearer's head when the laterally-extending members are in the spaced apart first open position and the head cradle is placed on the wearer's head.

17. The respirator of claim 16, wherein the means for securing and for manually disengaging the laterally-extending members in a spaced apart first open position comprises one or more snap buttons disposed on each side of the head cradle, a small ridge that is molded into one of the first and second laterally-extending members in position by acting as a catch, spring-loaded ball bearings that engage a recess in an adjacent laterally-extending member, plastic parts that create a spring loaded engaging action, hook and loop fasteners, or a tab that is deformable to hook around an edge of at least one of the laterally-extending members.

18. The respirator of claim 16, wherein a major surface of the first laterally-extending member faces a major surface of the second laterally-extending member in an overlapping relationship when in the second collapsed position.

19. The harness of claim 16, wherein a major surface of the first laterally-extending member faces a major surface of the second laterally-extending member in an overlapping relationship when the laterally-extending members are in the second location.

20. A harness for supporting a mask body on a person's face, which harness comprises:
  (a) a head cradle that has:
    (i) first and second laterally extending members; and
    (ii) a means for allowing the first and second laterally extending members to manually move from a first location to a second location, wherein the first and second laterally extending members are latched in the first location and are disengaged in the second location, wherein the first and second laterally-extending members each rest upon a wearer's head when the head cradle is placed thereon and the laterally-extending members are in the first location; and
  (b) one or more straps that are joined to the head cradle.

21. The respirator of claim 20, wherein the head cradle is made from a plastic selected from the group consisting of polypropylene, polyethylene, polyvinylchloride, and acrylonitrile-styrene-butadiene, and wherein the harness comprises first and second straps that are about 1 to 2 centimeters wide and up to 60 centimeters long.

22. The respirator of claim 20, wherein the laterally-extending members are capable of rotating about a point relative to one another.

23. The respirator of claim 20, wherein the latching of the laterally-extending members can be manually disengaged by a wearer.

* * * * *

UNITED STATES PATENT AND TRADEMARK OFFICE
CERTIFICATE OF CORRECTION

PATENT NO. : 8,839,785 B2  
APPLICATION NO. : 12/721036  
DATED : September 23, 2014  
INVENTOR(S) : David Castiglione et al.

Page 1 of 1

It is certified that error appears in the above-identified patent and that said Letters Patent is hereby corrected as shown below:

In the Claims

Column 7
Line 25, Claim 19, delete "harness" and replace with -- respirator --.

Signed and Sealed this
Seventh Day of April, 2015

Michelle K. Lee
*Director of the United States Patent and Trademark Office*

UNITED STATES PATENT AND TRADEMARK OFFICE
CERTIFICATE OF CORRECTION

PATENT NO.         : 8,839,785 B2                                Page 1 of 1
APPLICATION NO.    : 12/721036
DATED              : September 23, 2014
INVENTOR(S)        : David Castiglione et al.

It is certified that error appears in the above-identified patent and that said Letters Patent is hereby corrected as shown below:

In the Claims

Column 8
Line 16, Claim 21, delete "respirator" and replace with -- harness --.
Line 22, Claim 22, delete "respirator" and replace with -- harness --.
Line 26, Claim 23, delete "respirator" and replace with -- harness --.

Signed and Sealed this
Seventh Day of July, 2015

Michelle K. Lee
*Director of the United States Patent and Trademark Office*